(12) United States Patent
Ahiska

(10) Patent No.: US 9,364,571 B2
(45) Date of Patent: Jun. 14, 2016

(54) STERILIZATION WITH IN-LINE CONCENTRATING AND INJECTION OF HYDROGEN PEROXIDE

(75) Inventor: Fatih Ahiska, Ankara (TR)

(73) Assignee: GOA TEKNOLOJI DANISMANLIK ELEKTRONIK, IMALAT TICARET ITHALAT IHRACAT A.S., Ankara (TR)

( * ) Notice: Subject to any disclaimer, the term of this patent is extended or adjusted under 35 U.S.C. 154(b) by 464 days.

(21) Appl. No.: 13/437,035

(22) Filed: Apr. 2, 2012

(65) Prior Publication Data

US 2013/0302207 A1    Nov. 14, 2013

Related U.S. Application Data

(60) Provisional application No. 61/470,632, filed on Apr. 1, 2011.

(51) Int. Cl.
  *A61L 2/20*    (2006.01)

(52) U.S. Cl.
  CPC ............. *A61L 2/208* (2013.01); *A61L 2202/14* (2013.01); *A61L 2202/24* (2013.01)

(58) Field of Classification Search
  CPC .................................. A61L 2/20; A61L 2/208
  USPC ....................................................... 422/3, 28
  See application file for complete search history.

(56) References Cited

U.S. PATENT DOCUMENTS

| 4,169,123 | A | 9/1979 | Moore et al. |
| 4,169,124 | A | 9/1979 | Forstrom et al. |
| 4,642,165 | A | 2/1987 | Bier |
| 4,643,876 | A | 2/1987 | Jacobs et al. |
| 4,744,951 | A | 5/1988 | Cummings et al. |
| 4,756,882 | A | 7/1988 | Jacobs et al. |
| 4,956,145 | A | 9/1990 | Cummings et al. |
| 2003/0124026 | A1* | 7/2003 | Williams et al. ................ 422/33 |
| 2006/0078459 | A1* | 4/2006 | Kohler et al. ..................... 422/3 |

FOREIGN PATENT DOCUMENTS

WO    2005/067984 A1    7/2005

OTHER PUBLICATIONS

Beatriz Unger-˥-Bimczok, Volker Kottke, Christian Hertel, Johannes Rauschnabel, "The Influence of Humidity, Hydrogen Peroxide Concentration, and Condensation on the Inactivation of Geobacillus Stearothermophilus Spores with Hydrogen Peroxide Vapor", Journal of Pharmaceutical Innovation, vol. 3, No. 2 (Jun. 28, 2008), pp. 123-133.
James R. Rickloff "Factors Influencing Hydrogen Peroxide Gas Sterilant Efficacy", Advanced Barrier Inc. Nov. 12, 2008.

(Continued)

*Primary Examiner* — Sean E Conley
(74) *Attorney, Agent, or Firm* — Thomas | Horstemeyer, LLP

(57) ABSTRACT

In a hydrogen peroxide gas plasma sterilizer, the concentration of the hydrogen peroxide sterilant is an important factor in determining sterilization efficacy. The present application describes sterilizers, and sterilization methods, which use a novel injector-concentrator arrangement. This arrangement provides accurate control of concentration of the liquid-phase hydrogen peroxide, prior to vaporization of the liquid sterilant into the sterilization chamber. This increases the reliability and efficacy of the sterilization cycle.

22 Claims, 8 Drawing Sheets

(56) References Cited

OTHER PUBLICATIONS

Sterrad NX Sterilization System—User's Guide (REF 99920), Advanced Sterilization Products—a Johnson & Johnson Company, Division of Ethicon, Inc., Sep. 2008.
Sterrad 100NX Sterilizer System—User's Guide (REF 99970), Advanced Sterilization Products—a Johnson & Johnson Company, Division of Ethicon, Inc., Feb. 2008.
Sterrad 100 Sterilization System Service Guide, Advanced Sterilization Products Services, Inc., 1997.
Jacobs, Paul T., Sterrad 100S Sterilization System, Advanced Sterilization Products—a Johnson & Johnson Company, Division of Ethicon, Inc., 1999.
Sterrad 100NX Sterilization System—Service Troubleshooting Guide, Advanced Sterilization Products—a Johnson & Johnson Company, Division of Ethicon, Inc., Jun. 2007.

* cited by examiner

STERILIZATION WITH IN-LINE CONCENTRATING AND INJECTION OF HYDROGEN PEROXIDE

CROSS-REFERENCE

Priority is claimed from U.S. application 61/470,632 filed Apr. 1 2011, which is hereby incorporated by reference.

BACKGROUND

The present application relates generally to sterilization of objects, and more particularly to sterilization of medical apparatus using both hydrogen peroxide vapor and a glow discharge.

Note that the points discussed below may reflect the hindsight gained from the disclosed inventions, and are not necessarily admitted to be prior art.

Some background information can be found in the following documents, all of which are hereby incorporated by reference: Beatriz Unger-Bimczok, Volker Kottke, Christian Hertel, Johannes Rauschnabel, "The Influence of Humidity, Hydrogen Peroxide Concentration, and Condensation on the Inactivation of *Geobacillus stearothermophilus* Spores with Hydrogen Peroxide Vapor", Journal of Pharmaceutical Innovation, Vol. 3, No. 2 (28 Jun. 2008), pp. 123-133; James R. Rickloff "Factors Influencing Hydrogen Peroxide Gas Sterilant Efficacy", Advanced Barrier Inc. Nov. 12, 2008; U.S. Pat. Nos. 4,169,123, 4,169,124, 4,643,876, 4,756,882, 4,956,145, 4,642,165, and 4,744,951; PCT application WO 2005/067984; the Sterrad NX Sterilizer user and service manuals (from Advance Sterilization Products); and the Sterrad 100S Sterilizer user manual and service manuals.

Medical instruments were traditionally sterilized either with heat, such as is provided by steam, or a chemical, such as formaldehyde or ethylene oxide in the gas or vapor state. Each of these methods has drawbacks. Many medical devices, such as fiberoptic devices, endoscopes, power tools, etc. are sensitive to heat, moisture, or both. Formaldehyde and ethylene oxide are both toxic gases that pose a potential hazard to healthcare workers. Problems with ethylene oxide are particularly severe, because its use requires long aeration times to remove the gas from articles that have been sterilized. This makes the sterilization cycle time undesirably long.

Sterilization using liquid hydrogen peroxide solution has been found to require high concentration of sterilant, extended exposure time and/or elevated temperatures. However, sterilization using hydrogen peroxide vapor has been shown to have some advantages over other chemical sterilization processes (see, e.g., the '123 and '124 documents cited above).

The combination of hydrogen peroxide with a plasma provides certain additional advantages, as disclosed in the '876 document cited above. The '882 document cited above discloses the use of hydrogen peroxide vapor, generated from an aqueous solution of hydrogen peroxide, as a precursor of the reactive species generated by a plasma generator. The combination of hydrogen peroxide vapor diffusing into close proximity with the article to be sterilized and plasma acts to sterilize the articles, even within closed packages.

However, these methods of combining hydrogen peroxide vapor with a plasma, while useful in "open" systems, have been found to be inadequate to effect sterilization in articles having diffusion-restricted areas, since the methods are dependent upon diffusion of the sterilant vapor into close proximity with the article before sterilization can be achieved. Thus, in order to use these methods on articles with long, narrow lumens, it has been necessary to use high concentration of sterilant, extended exposure time, and/or elevated temperatures. For example, lumens longer than 40 cm and/or having an internal diameter of less than 0.4 cm have been particularly difficult to sterilize. Thus, no simple, safe, effective method of sterilizing longer and smaller lumens exists in the prior art.

The sterilization of articles containing diffusion-restricted areas, such as long narrow lumens, presents a special challenge for hydrogen peroxide vapor that has been generated from an aqueous solution of hydrogen peroxide, because: (i) water ($H_2O$) has a higher vapor pressure than hydrogen peroxide ($H_2O_2$), and will vaporize faster than hydrogen peroxide from an aqueous solution; (ii) water has a lower molecular weight than hydrogen peroxide and will diffuse faster than hydrogen peroxide in the vapor state.

Because of this, when an aqueous solution of hydrogen peroxide is vaporized, the innermost locations in a diffusion-restricted lumen will initially see an enhanced $H_2O:H_2O_2$ ratio. This can lead to condensation of water vapor on the surface of the material to be sterilized before sufficient impingement of hydrogen peroxide has reached the innermost locations. The liquid-phase water then becomes a barrier to the penetration of hydrogen peroxide vapor into diffusion-restricted areas, such as small crevices and long narrow lumens.

The '145 document cited above discusses the efficacy of highly concentrated hydrogen peroxide for the safe sterilization. The '067984 document discusses the problem of condensed water vapor blocking the diffusion of the sterilant to the bacteria lying on the surface of the material to be sterilized. The Unger document cited above explains the influence of humidity, hydrogen peroxide concentration, and the condensation of the water vapor in detail.

One cannot solve the problem by using more concentrated hydrogen peroxide, since concentrated solutions of hydrogen peroxide, i.e., greater than 60% by weight, can be hazardous, due to the oxidizing nature of the solution. Decomposition of liquid hydrogen peroxide is very exothermic, and releases large volumes of gas, so that stability is a serious concern. Highly-concentrated liquid hydrogen peroxide is so energetic that it has been used as a monopropellant for rocket engines. Moreover, highly concentrated hydrogen peroxide can form unstable reaction products with minor contaminants (such as fingerprint grease), and those reaction products can be a further source of instability.

The above-cited documents '165 (Bier) and '951 (Cummings et al.) both attempt to address this problem. Bier attempts to solve the problem by metering small increments of a hydrogen peroxide solution onto a heated surface to ensure that each increment is vaporized before the next increment is added. This helps to eliminate the difference in the vapor pressure and volatility between hydrogen peroxide and water, but it does not address the fact that water diffuses faster than hydrogen peroxide in the vapor state.

Cummings describes a process for concentrating hydrogen peroxide from a relatively dilute solution of hydrogen peroxide and water and supplying the concentrated hydrogen peroxide in vapor form to a sterilization chamber. The process involves vaporizing a major portion of the water from the solution and removing the water vapor produced before injecting the concentrated hydrogen peroxide vapor into the sterilization chamber as shown in FIG. 1A.

FIG. 1A shows the apparatus proposed by Cummings, which includes a vaporizing chamber 7 having any well-known means 3 for injecting into chamber 7 a predetermined amount of a solution of hydrogen peroxide and water. Chamber 7 may be controllably heated by any well-known means. Chamber 7 has an outlet port 2 through which vapors may be exhausted from chamber 7 by means of a vacuum. Port 2 may be opened or closed by valve 11. Chamber 7 also has an outlet port 14 leading through passage 6 to a sterilization chamber 8. Passage 6 may be open or closed by valve 5.

When valve 5 is closed and valve 1 is open; vacuum is applied to chamber 7 to evacuate air. Chamber 7 is heated until the desired temperature within chamber 7 is reached; that temperature is such that, when taken with the pressure within chamber 7, water in the form of vapor will be flashed from a solution of liquid hydrogen peroxide and water present in chamber 7. The process is initiated by the injection into evacuated chamber 7 of predetermined amount of a liquid solution of hydrogen peroxide and water through injection means 3. Conditions within chamber 7 cause the preferential vaporization of water from the solution and the vapor formed thereby is withdrawn from chamber 7 through port 2. At a point in time when a major portion of the water in the injected solution has been vaporized and withdrawn, but before a significant quantity of hydrogen peroxide has vaporized and been withdrawn, valve 1 is closed. What remains in chamber 7 is a hydrogen peroxide-water solution enriched in hydrogen peroxide, specifically greater than 40% hydrogen peroxide by weight, preferably 50 to 80% by weight. Vaporization of this enriched solution continues within chamber 7 and then valve 5 is opened to admit the vapors formed thereby to evacuated sterilization chamber 8. With a substantial amount of the water having been removed, the hydrogen peroxide vapor sterilant is able to disperse itself throughout the sterilizer and penetrate wraps and tubes without encountering a barrier effect that otherwise would have been present by reason of the effects of the present of water discussed above. Thus, the effective concentration of hydrogen peroxide vapor at the point of attack on the goods to be sterilized is markedly enhanced by the process.

Advance Sterilization Products, a division of Johnson and Johnson, introduced The Sterrad NX Sterilizer which employs Cummings method of delivering hydrogen peroxide to sterilize devices within the sterilization chamber. In this apparatus a 59% aqueous solution of hydrogen peroxide is injected into the delivery system condenser where it is condensed and concentrated and then introduced into the chamber. This modified process concentrates the 59% hydrogen peroxide to 90% nominal hydrogen peroxide (by selectively vaporizing and removing water) prior to being transferred into the sterilization chamber.

BRIEF DESCRIPTION OF THE DRAWINGS

The disclosed inventions will be described with reference to the accompanying drawings, which show important sample embodiments and which are incorporated in the specification hereof by reference, wherein.

DETAILED DESCRIPTION OF SAMPLE EMBODIMENTS

In a hydrogen peroxide gas plasma sterilizer, the concentration of the hydrogen peroxide sterilant is an important factor in determining sterilization efficacy. The present application describes sterilizers, and sterilization methods, which use a novel injector-concentrator arrangement. This arrangement provides accurate control of concentration of the liquid-phase hydrogen peroxide, prior to vaporization of the liquid sterilant for release into the sterilization chamber of the sterilizator. This increases the reliability and efficacy of the sterilization cycle.

This application describes new devices and methods which increase the reliability and efficacy of the sterilization cycle in an hydrogen peroxide gas plasma sterilization system by increasing and controlling the concentration of the liquid sterilant within the device, without requiring any handling or transportation of highly concentrated sterilant.

The numerous innovative teachings of the present application will be described with particular reference to presently preferred embodiments (by way of example, and not of limitation). The present application describes several inventions, and none of the statements below should be taken as limiting the claims generally.

The hydrogen peroxide gas plasma sterilization cycle is well understood and documented.

Figure 2:
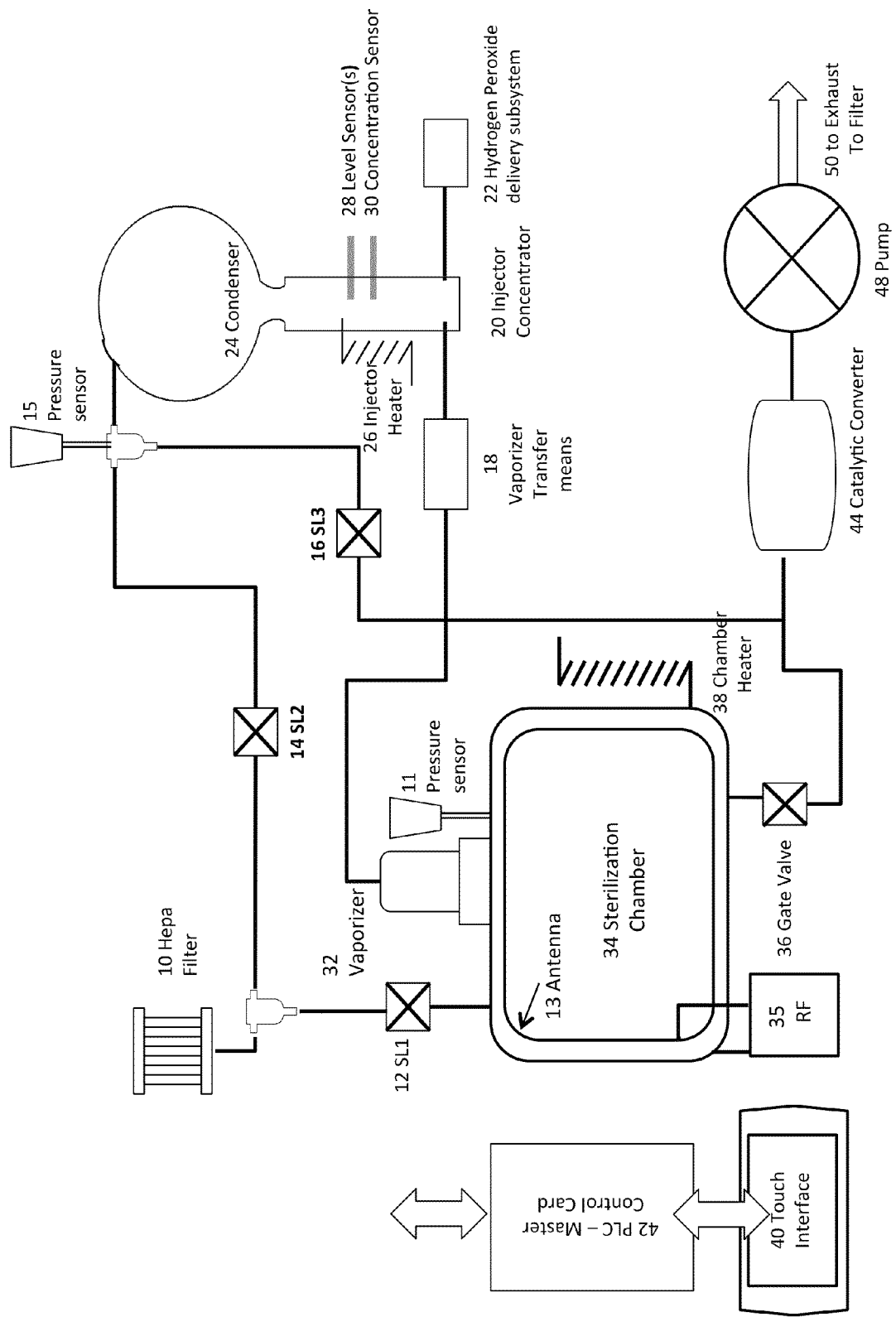
FIG. 2 shows the schematic of preferred embodiment of the hydrogen peroxide injector concentrator as deployed in a typical sterilizer configuration.
Figure 3:
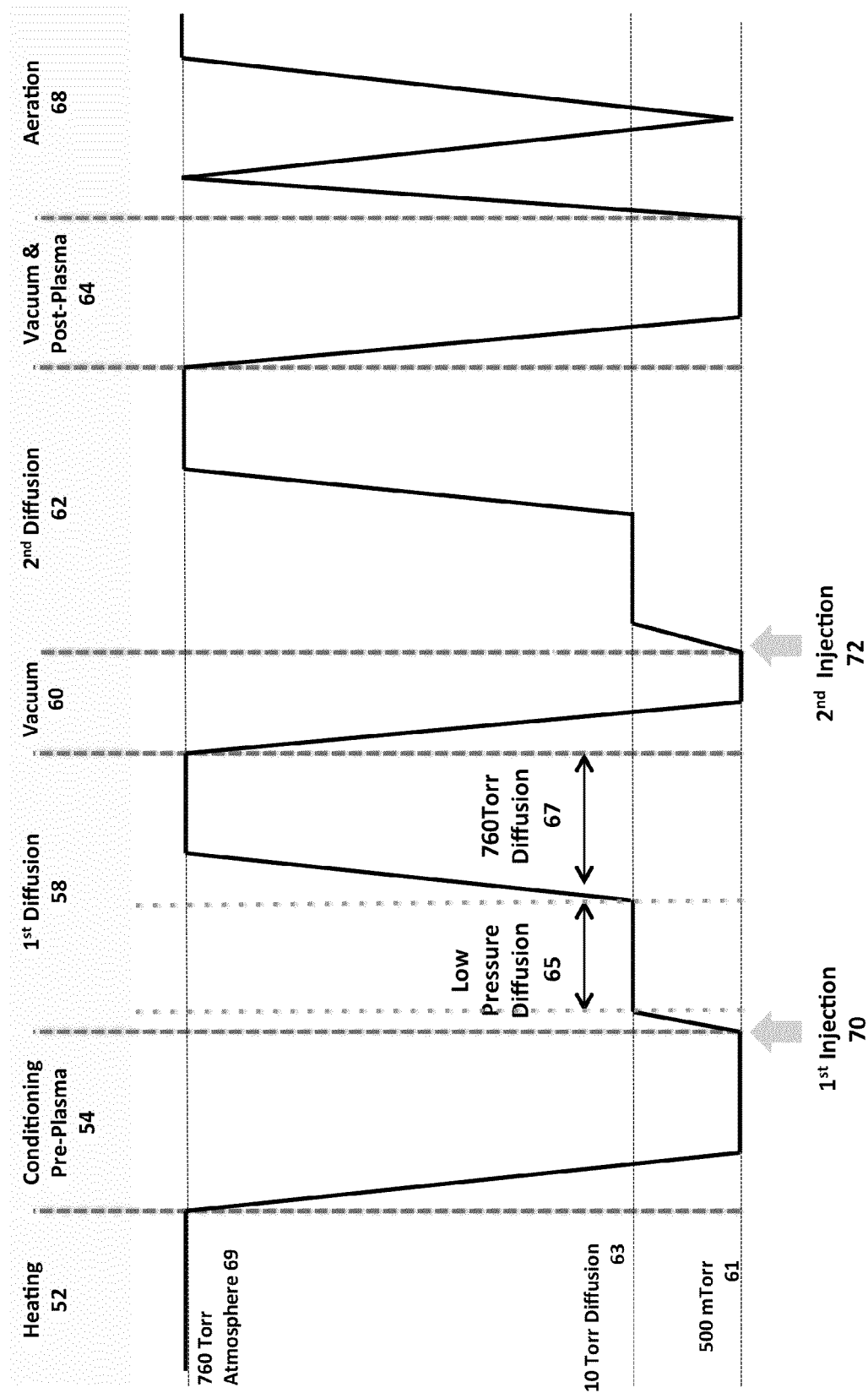
FIG. 3 shows pressure curve within the sterilization chamber during a typical hydrogen peroxide gas plasma sterilization cycle.

FIG. 2 shows the schematic of preferred embodiment of the hydrogen peroxide injector-concentrator as deployed in a typical sterilizer, and FIG. 3 shows the state of the sterilization chamber during a typical sterilization cycle. In a typical cycle the washed and dried medical instruments to be sterilized are packed into sealed tyvek pouches and placed into the heated sterilization chamber 34 of the sterilizer. During the heating process 52 the temperature within the chamber is increased to around 48-55 degree centigrade. Depending on the power consumption of the heating resistance 38, this process can take e.g. 10-15 minutes.

The chamber pressure is then lowered sufficiently low to start a plasma within the chamber by an RF generator attached to antenna 13 and the chamber 34. Preferable the chamber pressure should be below 500 mT during this plasma pre-conditioning phase 54. The chamber pressure is monitored via a pressure gauge 11. The plasma generated within the chamber generates and distributes heat within the chamber and further ensures evaporation of any residual water from the medical instruments.

After pre-conditioning liquid hydrogen plasma is injected (70) into a pre-heated vaporizer 32 intermittently in small volumes say in 6-20 pulses with 8-15 sec duration between the pulses in between. The benefits of the pulsed injection are described in the Cummings' US patent. In the vaporizer the sterilant is converted into vapor which is then released to the sterilization chamber.

The chamber is then kept at approximately 10-20 Torr pressure to allow diffusion for a period of low pressure diffusion 65. Typically this process lasts about for approximately 6-8 minutes. During this period hydrogen peroxide vapor is expected to diffuse homogenously inside the chamber and into the medical instruments in the $H_2O_2$ permeable pouches. During the diffusion 58 the sterilization chamber 34 temperature and pressure are the critical parameters effecting the sterilization cycle efficacy and controlled by well known means and in a well known process.

Later, conditioned air is introduced through a HEPA filter 10 into the chamber via electrically controlled solenoids SL1 (12) and the chamber pressure is raised up to atmospheric pressure 69 which is kept stable for 760 Torr diffusion period 67 of about 2-15 minutes depending on the lumen length of the medical instruments. A short duration may not be sufficient for hydrogen peroxide molecules to penetrate a lumen despite the increased pressure. The optimum diffusion duration for a given lumen and for a device is established empirically by exhaustive tests carried out by following the half cycle validation guidelines provided by ISO 14937 standards.

This cycle then repeated for further sterilization assurance (see FIG. 3), e.g. vacuuming 60, followed by 2nd injection 72 and 2nd diffusion 62. This phase is followed by evacuation to low vacuum 64 and application of RF energy to generate plasma. The plasma ensures hydrogen peroxide molecules left in the chamber and on the pouches to be decomposed into free radicals and eventually water and oxygen. The free radicals thus generated together with the UV radiated from the plasma further improve the sterilization efficacy.

At the final aeration phase 68 ventilates the chamber and further ensures that the medical equipment to be sterilized is cleaned from any residual excess hydrogen peroxide. During the evacuation any remaining hydrogen peroxide molecules that left the chamber are trapped within the catalytic converter 44 before extracted by the pump 48 and exhausted via a filter 50.

In the preferred embodiment described above SL1 (12), SL2 (14), SL3 (16) are two way valves used to prevent or admit the flow of liquid, vapor and pure air controlled by dedicated computer, the master controller card 42 which receives input commands via touch sensitive screen graphical user interface 40. These solenoids are chemically resistive to hydrogen peroxide transmission.

In the plasma sterilizer depicted in FIG. 2, the hydrogen peroxide delivery sub-system 22 delivers a low concentration sterilant liquid from a small container or cartridge to the injector concentrator 20. The concentration of the sterilant within the container or cartridges are kept below 60% due to transport restriction. The delivery process is a well know art and usually involves filling up the injector until a level sensor 28 provides a signal to the master controller 42. It would be possible to fill the injector by transferring the liquid via a small pump with associated precision volumetric control unit.

In one embodiment the level detection within the injector is performed by placing two stainless steel metal pins opposing to each other with a thickness less than 1 mm to measure resistivity of the medium. If both pins are in hydrogen peroxide liquid then it would present a corresponding circuit a lower resistance.

In one embodiment, if there is an overfill then the solenoid SL2 (73) and solenoid SL3 (75) could be used to make further fine adjustments. For this purpose the SL3 could provides low vacuum suction option as it is connected to the evacuating pump 49 via catalytic converter 44 whereas the SL2 provides atmospheric pressure. By controlling these solenoids in harmony with two way hydrogen peroxide delivery system 89 it is possible to adjust the liquid level via relatively simple and well understood art.

In the disclosed inventions, the concentration of the hydrogen peroxide is a critical parameter. The disclosed injector concentrator (shown separately in FIG. 4A) is used to control this critical parameter. Within this unit the sterilants concentration is increased in a controlled manner up to a pre-determined level say around 85-90% weight.

During the concentration process the injector concentrator is kept heated in a standby mode via injector heater 93. Once a fixed amount of sterilant (say 6 ml for a sterilizer with a 110 liter sterlization chamber) has filled into the injector, then the pressure of the concentrator is reduced by intermittently opening and closing SL3 (75). Concurrently the injector heater 93 power is increased to force the liquid sterilant to boil. By controlling the condenser pressure via monitoring the pressure sensor (95) and power input to the heater 93 it is possible to create conditions where major portion of the water within the sterilant is vaporized. The water vapor is then suctioned out via the suction solenoid SL3 (75) intermittently. The condenser is kept at the ambient temperature which creates a temperature gradient encouraging any escaping hydrogen peroxide to condense and return back to the injector while due to low pressure, water continues to remain in vapor phase.

During concentration process the concentration is continuously monitored by measuring the electrical resistance of the hydrogen peroxide via sensors placed in the injector.

Figure 5:
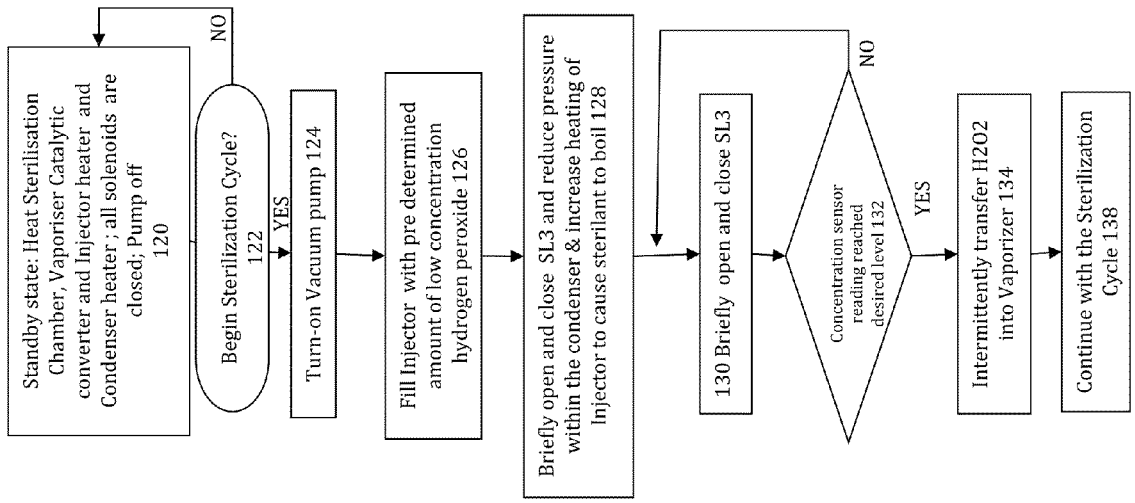
FIG. 5 shows a flow chart of the operation of the injector-concentrator in a preferred embodiment.

FIG. 5 depicts the flow chart of the preferred concentration process. Typically during the standby state of the sterilizer the sterilization chamber, vaporizer, catalytic converter and Injector concentrator are kept heated at predetermined levels. All solenoids SL1, SL2 and SL3 are closed and the pump is turned off.

The process usually starts after the medical instruments are loaded into the sterilization chamber and the door is securely locked via a command on the touch screen attached to the device. Once the "begin sterilization Cycle" command is received 122 the vacuum pump is turned on 124 and subsequently the hydrogen peroxide delivery subsystem delivers pre-determined amount of low concentration hydrogen peroxide liquid into the injector concentrator 126. The injector heater power is increased from standby to a higher operational power and the solenoid SL3 (16) is briefly opened and closed intermittently (said brief period which can be determined empirically) to lower the pressure of the condenser and cause the sterilant to boil 128. Once the critical low pressure and high temperature is reached the hydrogen peroxide within the injector boils and preferentially water vapor is extracted from the condenser chamber. At this stage it would be beneficial to monitor the condenser pressure via a sensor and continue the SL3 process until the pre-determined pressure is reached.

The solenoid SL3 (16) is further opened and closed intermittently for a brief period to extract vapor wherein said brief period which can be determined empirically. Following this the concentration sensor reading is taken to examine whether the desired concentration level is reached 132. If not reached, then the SL3 operation mention in this paragraph is repeated.

The duration of the concentration process can be determined by continuously checking whether the desired concentration level has been reached via well know sensor means.

In the preferred embodiment the electrical resistance characteristics of the hydrogen peroxide is continuously monitored and upon reaching a desired level around 85-90% wt the concentration is terminated.

Once the desired concentration level of the sterilant is reached then the liquid sterilant is transferred intermittently into the vaporizer 134 and the diffusion cycle of the sterilization starts 138.

The hydrogen peroxide sterilant is usually supplied with various amounts of stabilizers (phosphate derivatives etc.) which can vary its electrical resistance characteristics, and the rate of its electrical resistance varies with concentration. In the preferred embodiment the electrical characteristics of the particular sterilant used are drawn as a plot against the concentration level. The concentration of the $H_2O_2$ can be measured independently via a densitometer or any other well known means.

In another embodiment the electrical resistance characteristic of the hydrogen peroxide is continuously monitored, and upon reaching a desired level around 87-92% wt the concentration is terminated.

In another embodiment the concentration process is terminated when a predetermined volume or weight of sterilant remains in the injector. At this point the boiling process in the injector can be stopped. The volume of the hydrogen peroxide is measured via electrical level sensors or weight sensors or optically or other well known means. This predetermined volume can be established empirically via repeated experiments involving measuring the density of the remaining liquid sterilant versus the volume and weight (or both) of the remaining sterilant while keeping the concentration process parameters unchanged.

In another embodiment the concentration process is terminated after a fixed duration. This fixed duration can be established empirically by repeated experiments to extract typical durations required to reached desired concentrations.

Figure 4:
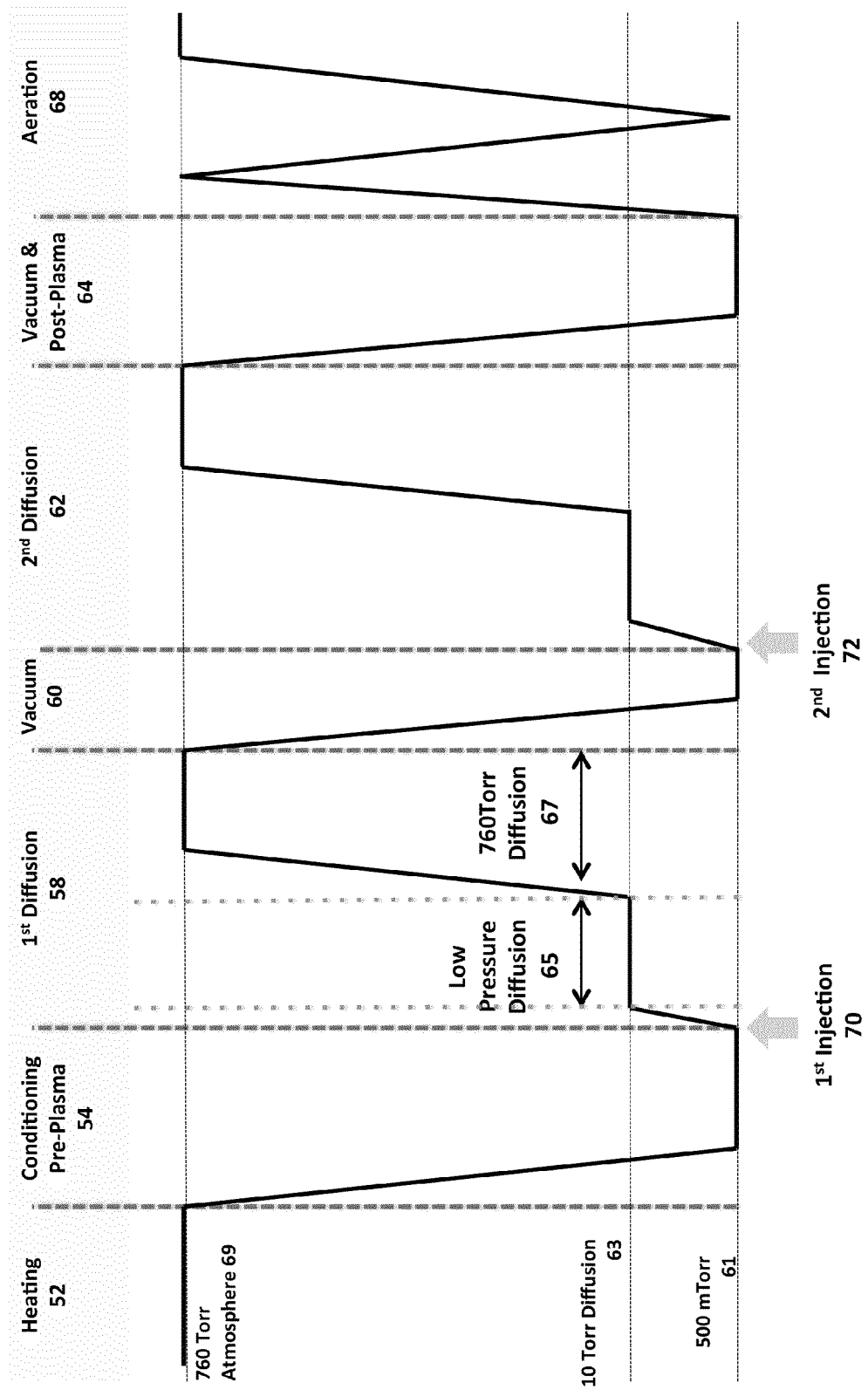
FIG. 4A shows an injector-concentrator embodiment.
FIG. 4B shows an alternative injector-concentrator embodiment.
Figures 4A, 4B:
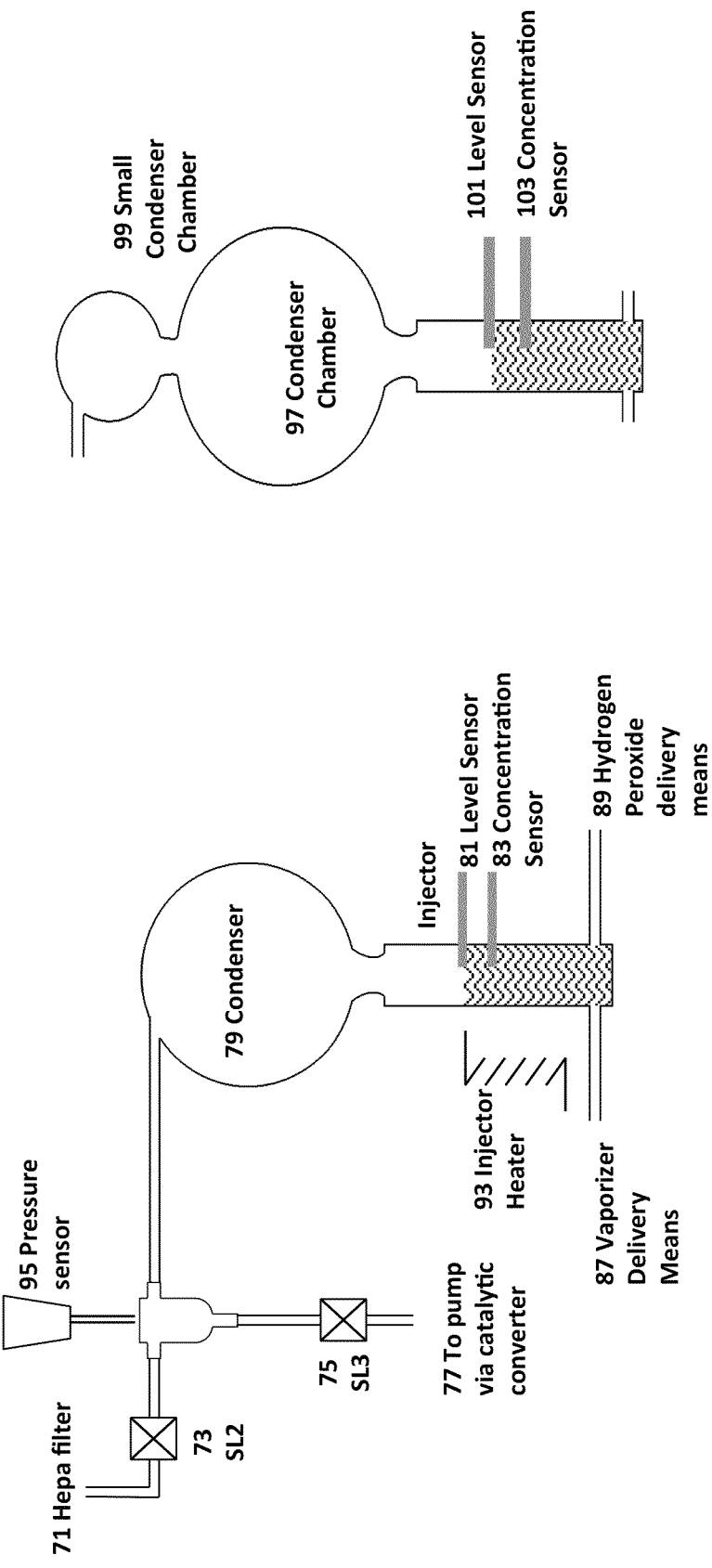

FIG. 4B shows the schematic of another embodiment of the injector concentrator wherein the main condenser chamber 97 is complemented by a secondary small condenser chamber 99 which can provide better condensation efficiency. Liquid concentration is a well known art, and the shape and material of the injector concentrator can be designed to further improve the concentration efficiency and hence reduce the duration of the process.

Figure 1:
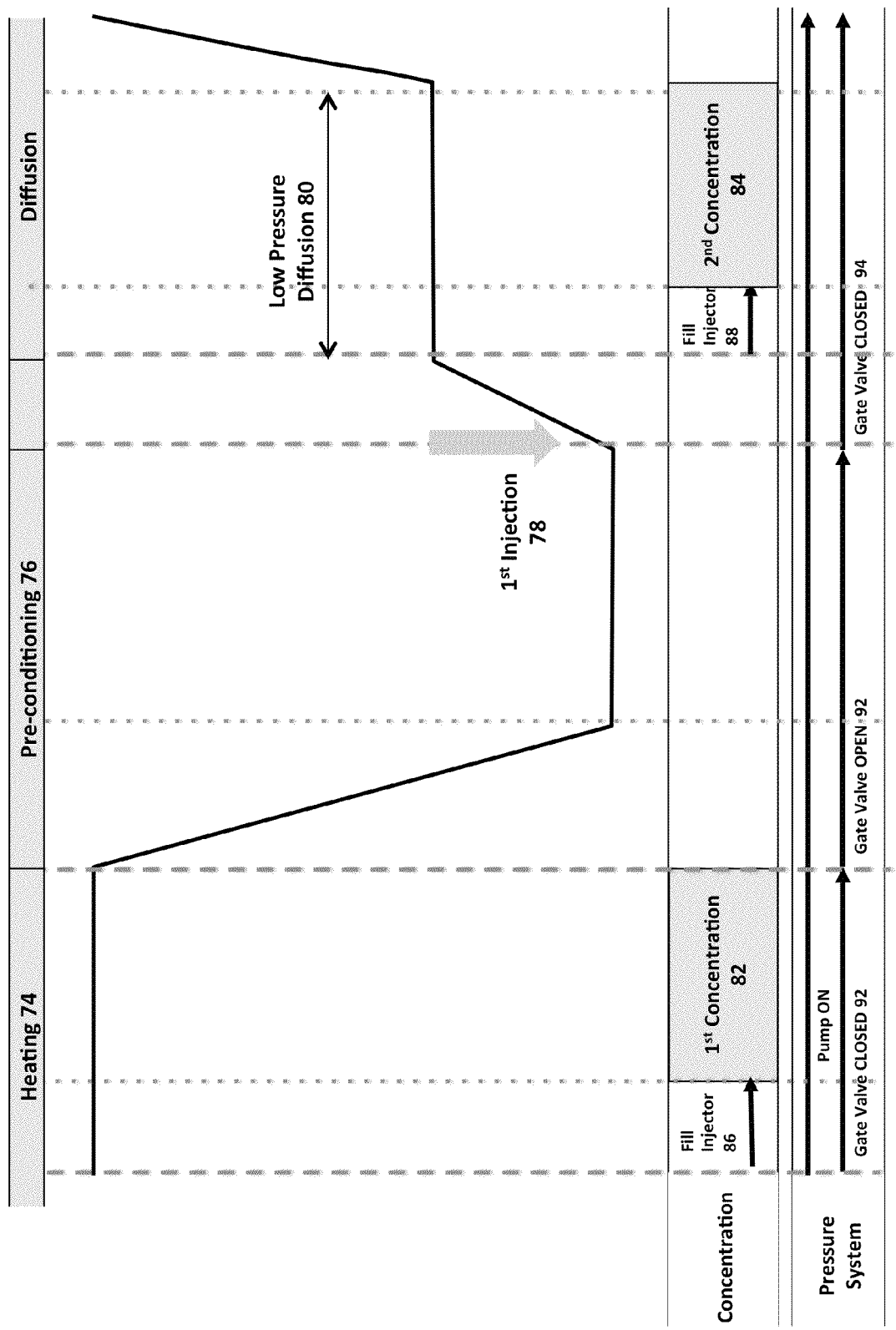
FIG. 1 schematically shows integration of a separate hydrogen peroxide concentration into a typical hydrogen peroxide gas plasma sterilization cycle.
Figure 1A:
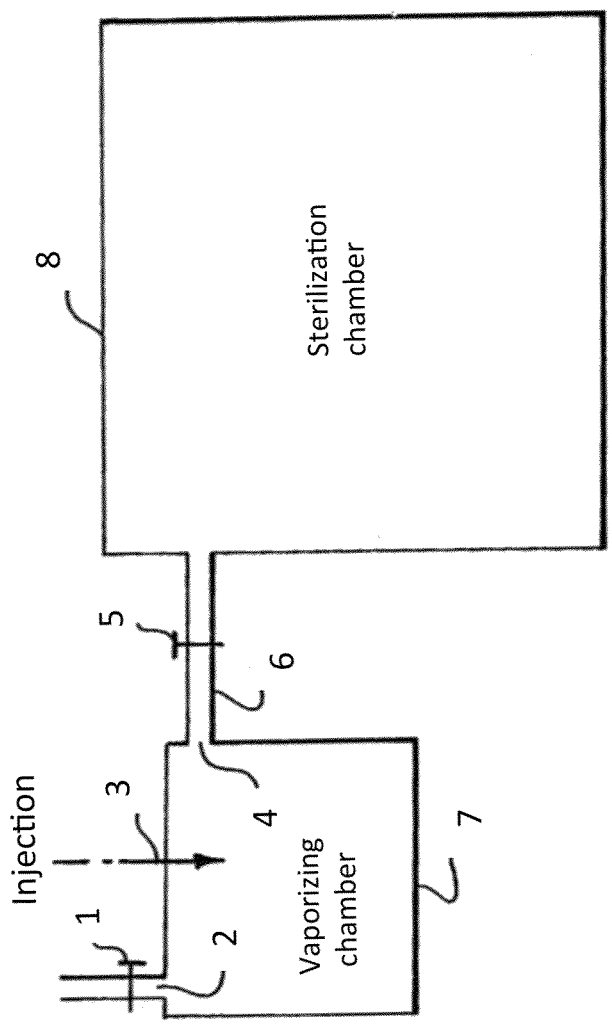
FIG. 1A shows a previously proposed apparatus to concentrating a liquid hydrogen peroxide solution.

As presented earlier in a plasma sterilizer the sterilization cycle is repeated twice for sterilization assurance. In the example of FIG. 1, the concentration process 82 for the first injection 78 is carried out during heating of the sterilization chamber 74. During the heating the gate valve 36 is closed 92 the pump 48 is turned on 90 and the injector is filled 86 and the concentration process 82 begins. In the preferred embodiment the second concentration for the second cycle is performed during the low pressure 1st diffusion 80 which typically lasts 8 minutes and provides sufficient time for the concentration process.

In another embodiment it is possible to concentrate the sterilant at double volume which would be sufficient for two injections. In this case the injector concentrator would be designed to hold double amount of sterilant and Vaporizer delivery means 18 only delivers the half of the volume of the concentrated sterilant at each injection.

Figure 6:
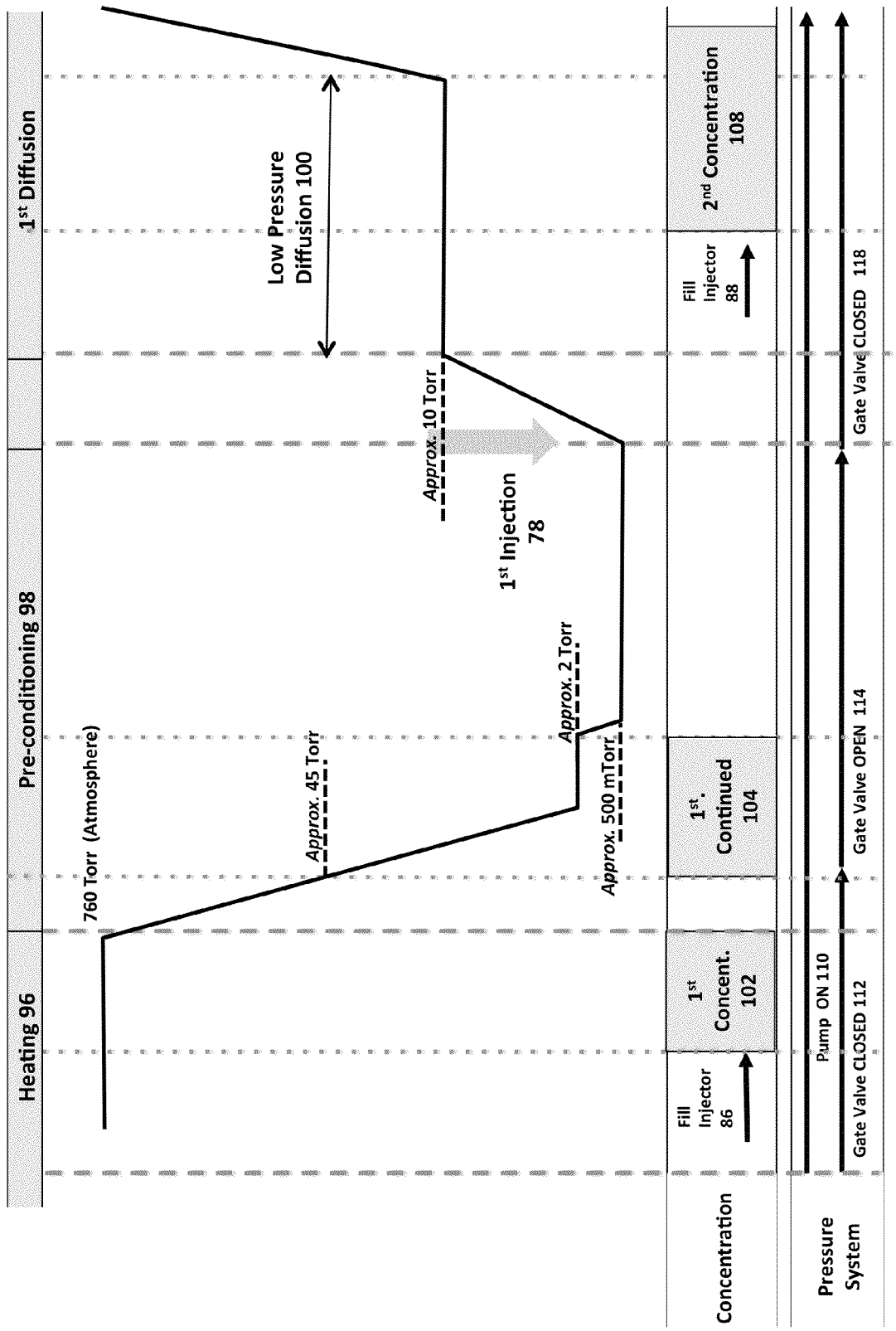
FIG. 6 shows an alternative integration of the hydrogen peroxide concentration into a typical hydrogen peroxide gas plasma sterilization cycle.

FIG. 6 shows an alternative integration of the hydrogen peroxide concentration process into the first sterilization cycle. In this embodiment in order to further reduce the sterilization cycle duration, the concentration process is performed partially during the heating 96 and partially during a portion of the pre-conditioning 98. Because there is only one pump employed which is used for both evacuating the air from the chamber 44 as well as the condenser 24, once the gate valve 36 is opened then the solenoid SL3 becomes ineffective. In this embodiment the concentration process can resume 104 when the chamber pressure drops down to say 45 Tor. During the concentration 104 it may not be possible to bring the chamber pressure low enough for the plasma to trigger since the gate vane is open and the water vapor is suctioned from the condenser. However once the concentration is finished the chamber pressure can be brought down to say 500 mT and the plasma starts.

Further in the preferred embodiment it is possible to start continue the 2nd concentration 108 even after raising the chamber pressure to the atmospheric level for the high diffusion as depicted in FIG. 6. This scheme offers a solution if the low pressure diffusion duration 107 is too short to accommodate the second concentration 108.

In another embodiment the evacuation of the condenser chamber of the injector concentrator is done by employing a separate pump other than the pump used to evacuate the sterilization chamber. This would allow greater flexibility in deciding the start time of the concentration process. The evacuated vapor does still need through the catalytic converter to trap any hydrogen peroxide which escapes the condenser.

The preferred embodiment has been implemented and tested in Stericool 110S model from GOA Technologies. It has been validated that consistently high concentration level achieved (85-90%) contributed significantly to the sterilization efficacy of the device particularly when used with long lumens. The extent of penetration of hydrogen peroxide into a tube is measured by colorimetrically assaying the amount of hydrogen peroxide deposited on the special purpose hydrogen peroxide chemical indicators placed in standard lumen set.

The disclosed innovations, in various embodiments, provide one or more of at least the following advantages. However, not all of these advantages result from every one of the innovations disclosed, and this list of advantages does not limit the various claimed inventions.

Faster throughput;
Better than $10^{-6}$ sterilization;
Shorter cycle time;
Better safety;
Lower cost of consumables;
Better results with articles having long thin lumens;
Faster process with articles having long thin lumens;
Reduced likelihood of handling toxic exhaust and/or byproduct;
Fewer uncontrolled process variables; and/or
Fewer safety concerns.

According to some but not necessarily all embodiments, there is provided: A process for introducing concentrated hydrogen peroxide vapor to interior surfaces of medical instruments with lumens in an evacuated sterilization chamber comprising the steps of: filling an injector concentrator at a predetermined volume of liquid solution of relatively dilute hydrogen peroxide; heating the injector concentrator and evacuating its condenser chamber to preferentially vaporize the water content of the said liquid into a condenser prior to vacuuming said sterilization chamber; intermittently withdrawing a portion of said water vapor from said condenser chamber via vacuum suction to concentrate said hydrogen peroxide remaining in said injector concentrator; terminating said withdrawal of water vapor from said condenser chamber when said remaining hydrogen peroxide is measured to be sufficiently concentrated so as to produce, concentrated hydrogen peroxide greater than about 80% by weight; intermittently transferring the said concentrated hydrogen peroxide liquid in small volumes into a separate pre heated vaporizer connected to the sterilization chamber; and maintaining said hydrogen peroxide vapors in contact with said medical instruments until sterilization is achieved.

According to some but not necessarily all embodiments, there is provided: A sterilization process, comprising the steps, in any order unless specifically stated, of: placing objects to be sterilized into a sterilization chamber; performing a low-pressure evaporation procedure on an initial volume of aqueous hydrogen peroxide which has an initial concentration of less than about 60% wt hydrogen peroxide, to extract water vapor therefrom, without passing the water vapor through the sterilization chamber, until the resulting concentrated hydrogen peroxide is measured to have reached at least a target concentration value; said target concentration value being greater than 80% wt; evacuating said sterilization chamber, and generating a plasma in a space which is continuous with said sterilization chamber for a period; and then vaporizing at least some of the concentrated hydrogen peroxide into said sterilization chamber; holding said sterilization chamber at a pressure of less than 50 Torr for more than 3 minutes, while said concentrated hydrogen peroxide remains present in the vapor phase; and then rapidly increasing the pressure of said sterilization chamber, whereby a net flow of concentrated hydrogen peroxide vapor into the interior of lumens of said objects occurs; wherein said concentrating and vaporizing steps are performed at different locations within a single machine According to some but not necessarily all embodiments, there is provided: A sterilization process, comprising the steps, in any order, of: placing objects to be sterilized into a sterilization chamber; performing a low-pressure evaporation procedure on an initial volume of aqueous hydrogen peroxide to extract water vapor therefrom until the resulting concentrated hydrogen peroxide is known to have reached at least a target concentration value; said target concentration value being greater than 80% wt; evacuating said sterilization chamber; transferring at least some of said concentrated hydrogen peroxide into a vaporizer, and vaporizing at least some of the concentrated hydrogen peroxide from said vaporizer into said sterilization chamber; and holding said sterilization chamber at a pressure of less than 50 Torr for more than 3 minutes, while said concentrated hydrogen peroxide remains present in the vapor phase; wherein said concentrating and vaporizing steps are performed within a single machine According to some but not necessarily all embodiments, there is provided: A sterilization process, comprising the steps, in any order, of: placing objects to be sterilized into a sterilization chamber; concentrating aqueous hydrogen peroxide until the resulting concentrated hydrogen peroxide is known to have reached at least a target concentration value; said target concentration value being greater than 80% wt; evacuating said sterilization chamber, and vaporizing at least some of the concentrated hydrogen peroxide into said sterilization chamber at less than 50 Torr for a duration and then rapidly increasing the pressure of said sterilization chamber, whereby a net flow of concentrated hydrogen peroxide vapor into the interior of lumens of said objects occurs; wherein said concentrating and vaporizing steps are performed by different parts of a single machine.

According to some but not necessarily all embodiments, there is provided: A sterilization process, comprising the steps, in any order, of: placing objects to be sterilized into a sterilization chamber; concentrating aqueous hydrogen peroxide until the resulting concentrated hydrogen peroxide is known to have reached at least a target concentration value; said target concentration value being greater than 80% wt; evacuating said sterilization chamber, generating a plasma within said chamber for a determined duration, and then vaporizing at least some of the concentrated hydrogen peroxide into said sterilization chamber; and holding a concentrated hydrogen peroxide vapor in said chamber, for long enough to reduce the population bacteria therein by at least a factor of a million; wherein said concentrating and vaporizing steps are performed within a single machine According to some but not necessarily all embodiments, there is provided: A sterilization system, comprising, in a single unit: a sterilization chamber; a concentrator which performs a low-pressure evaporation procedure on an initial volume of aqueous hydrogen peroxide, to extract water vapor therefrom until the resulting concentrated hydrogen peroxide is known to have reached at least a target concentration value; said target concentration value being greater than 80% wt; a vaporizer, which vaporizes at least some of the concentrated hydrogen peroxide into said sterilization chamber; and a valve from said chamber to a vacuum manifold, and another valve from said concentrator to said vacuum manifold; wherein said concentrating and vaporizing steps are performed within a single machine.

According to some but not necessarily all embodiments, there is provided: sterilizers, and sterilization methods, which use a novel injector-concentrator arrangement. This arrangement provides accurate control of concentration of the liquid-phase hydrogen peroxide, prior to vaporization of the liquid sterilant into the sterilization chamber. This increases the reliability and efficacy of the sterilization cycle.

Modifications and Variations

As will be recognized by those skilled in the art, the innovative concepts described in the present application can be modified and varied over a tremendous range of applications, and accordingly the scope of patented subject matter is not limited by any of the specific exemplary teachings given. It is intended to embrace all such alternatives, modifications and variations that fall within the spirit and broad scope of the appended claims.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A process for introducing concentrated hydrogen peroxide vapor to interior surfaces of medical instruments with lumens in an evacuated and pre-heated sterilization chamber comprising the steps of:
    filling an injector concentrator at a predetermined volume of liquid solution of hydrogen peroxide which has a concentration below 60% wt;
    heating and lowering the pressure in said injector concentrator to vaporize portion of said liquid solution while intermittently withdrawing a portion of the resulting vapor from said injector concentrator, wherein said withdrawing uses a vacuum pump bypassing said sterilization chamber, wherein said vaporizing of portion of liquid solution produces more water vapor than hydrogen peroxide vapor, and wherein pressure in said sterilization chamber is independent to the pressure in said injector concentrator during vaporization;
    terminating said withdrawal of vapor from said injector concentrator when remaining concentrated hydrogen peroxide liquid reaches a preset concentration level greater than above 80% wt in said injector concentrator;
    starting diffusion by intermittently transferring said concentrated hydrogen peroxide liquid in small volumes into a separate pre heated vaporizer connected to said sterilization chamber to produce hydrogen peroxide vapor; and maintaining said hydrogen peroxide vapor in contact with said medical instruments until sterilization is achieved.

2. The process of claim 1 wherein said preset concentration level of hydrogen peroxide is in the range of 80 to 94% wt.

3. The process of claim 1 wherein measurement of the concentration level of said concentrated hydrogen peroxide liquid is performed by measuring the electrical resistance characteristics of said concentrated hydrogen peroxide liquid or by measuring the remaining volume or weight of said concentrated hydrogen peroxide liquid left in said injector concentrator.

4. The process of claim 1 wherein measurement of the concentration level of said concentrated hydrogen peroxide liquid is performed by terminating the concentration process after a preset time.

5. The process of claim 1 wherein the pressure of said sterilization chamber is reduced using a separate pump to said vacuum pump used for said withdrawing.

6. The process of claim 1 wherein said process has two or more diffusions, and wherein measurement of the concentration level of hydrogen peroxide liquid for use for a second diffusion is performed partially during a low pressure phase of a first diffusion.

7. The process of claim 1 wherein said process has two or more diffusions, and wherein measurement of the concentration level of hydrogen peroxide liquid for use for a first diffusion is performed during a pre-conditioning phase.

8. A sterilization process, comprising the steps of:
placing objects to be sterilized into a sterilization chamber;
followed by the steps of, in any sequential or partly concurrent order:
  performing a low-pressure evaporation procedure to extract water vapor from an initial volume of aqueous hydrogen peroxide with an initial concentration of less than 60% wt hydrogen peroxide until the resulting concentrated hydrogen peroxide liquid is measured to have reached at least a target concentration value, wherein said extracted water vapor does not pass through said sterilization chamber, and wherein said target concentration value is greater than 80% wt;
  evacuating said sterilization chamber, and generating a plasma in a space which is continuous with said sterilization chamber, wherein the pressure in said sterilization chamber is independent to the pressure used in said evaporation procedure;
followed by the steps of:
  vaporizing at least some of said concentrated hydrogen peroxide liquid into said sterilization chamber;
  maintaining said sterilization chamber at a pressure and temperature for more than 3 minutes so that said concentrated hydrogen peroxide remains at least partly present in the vapor phase; and
  rapidly increasing the pressure of said sterilization chamber, whereby a net flow of concentrated hydrogen peroxide vapor into the interior of lumens of said objects occurs;
  wherein said concentrating and vaporizing steps are performed at different locations within a single machine.

9. The process of claim 8, wherein said target concentration is greater than 85% wt.

10. The process of claim 8, wherein the electrical resistivity of the concentrated hydrogen peroxide liquid is measured.

11. The process of claim 8, wherein the volume of the concentrated hydrogen peroxide liquid is measured.

12. The process of claim 8, wherein said evacuating step evacuates said sterilization chamber to less than 1 Torr.

13. A sterilization process, comprising the steps of:
placing objects to be sterilized into a pre-heated sterilization chamber;
followed by the steps of, in any sequential or partly concurrent order:
  performing a low-pressure evaporation procedure on an initial volume of aqueous hydrogen peroxide to extract water vapor therefrom until the resulting concentrated hydrogen peroxide is known to have reached at least a target volume, wherein said target volume corresponds to a target concentration value greater than 80% wt;
  evacuating said sterilization chamber, wherein the pressure in said sterilization chamber is independent to the pressure used in said evaporation procedure;
followed by the steps of:
  transferring at least some of said concentrated hydrogen peroxide into a vaporizer, and vaporizing at least some of said concentrated hydrogen peroxide from said vaporizer into said sterilization chamber; and
  maintaining said sterilization chamber at a pressure and temperature for more than 3 minutes so that said concentrated hydrogen peroxide remains at least partly present in the vapor phase;
  wherein said concentrating and vaporizing steps are performed within a single machine.

14. The process of claim 13, wherein said target concentration is greater than 85% wt.

15. The process of claim 13, wherein said evacuating step reaches a pressure of less than 1 Torr.

16. The process of claim 13, wherein said concentrating step is timed.

17. The process of claim 13, wherein said vaporizing step is a flash boiling step.

18. The process of claim 13, further comprising the additional step, after the start of said evacuating step and before the end of said vaporizing step, of initiating a glow discharge in a volume which is continuous with said chamber.

19. A sterilization process, comprising the steps of:
placing objects to be sterilized into a pre-heated sterilization chamber;
followed by the steps of, in any sequential or partly concurrent order:
  concentrating aqueous hydrogen peroxide until the resulting concentrated hydrogen peroxide is known to have reached at least a target concentration value, wherein said target concentration value is greater than 80% wt;
  evacuating said sterilization chamber, wherein the pressure in said sterilization chamber is independent to the pressure used for said concentrating step;
followed by the steps of:
  vaporizing at least some of said concentrated hydrogen peroxide into said sterilization chamber at less than atmospheric pressure;
  holding concentrated hydrogen peroxide vapor in said chamber for long enough to reduce the population bacteria therein by at least a factor of a million; and
  rapidly increasing the pressure of said sterilization chamber, whereby a net flow of concentrated hydrogen peroxide vapor into the interior of lumens of said objects occurs;
  wherein said concentrating and vaporizing steps are performed by different parts of a single machine.

20. The process of claim 19, wherein said target concentration is greater than 85% wt.

21. A sterilization process, comprising the steps of:

placing objects to be sterilized into a pre-heated sterilization chamber;

followed by the steps of, in any sequential or partly concurrent order:

concentrating aqueous hydrogen peroxide until the resulting concentrated hydrogen peroxide is known to have reached at least a target concentration value, wherein said target concentration value is greater than 80% wt;

evacuating said sterilization chamber, wherein the pressure in said sterilization chamber is independent to the pressure used for said concentrating step;

followed by the steps of:

generating a plasma in said chamber for a pre determined duration;

vaporizing at least some of the concentrated hydrogen peroxide into said sterilization chamber; and holding a concentrated hydrogen peroxide vapor in said chamber for long enough to reduce the population bacteria therein by at least a factor of a million;

wherein said concentrating and vaporizing steps are performed within a single machine.

22. The process of claim 21, wherein said target concentration is greater than 85% wt.

\* \* \* \* \*